US007752916B2

(12) United States Patent
Han et al.

(10) Patent No.: US 7,752,916 B2
(45) Date of Patent: Jul. 13, 2010

(54) APPARATUS AND METHOD FOR MATERIAL TESTING OF MICROSCALE AND NANOSCALE SAMPLES

(75) Inventors: Jong H. Han, Pataskala, OH (US); M. Taher A. Saif, Champaign, IL (US); Michael D. Uchic, Dayton, OH (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 451 days.

(21) Appl. No.: 11/897,927

(22) Filed: Aug. 31, 2007

(65) Prior Publication Data

US 2010/0064765 A1     Mar. 18, 2010

(51) Int. Cl.
*G01D 1/16* (2006.01)
*G01L 7/00* (2006.01)

(52) U.S. Cl. .......................................... 73/789; 73/856
(58) Field of Classification Search ................... 73/788, 73/789, 790, 856, 859
See application file for complete search history.

(56) References Cited

U.S. PATENT DOCUMENTS

| | | | |
|---|---|---|---|
| 4,784,720 A | 11/1988 | Douglas | |
| 4,855,017 A | 8/1989 | Douglas | |
| 5,501,893 A | 3/1996 | Laermer et al. | |
| 6,170,332 B1 | 1/2001 | MacDonald et al. | |
| 6,230,571 B1 | 5/2001 | Kimerer, Jr. | |
| 6,240,782 B1 | 6/2001 | Kato et al. | |
| 6,606,913 B1 | 8/2003 | Gianchandani | |
| 6,817,255 B2 * | 11/2004 | Haque et al. ........... 73/862.638 |

FOREIGN PATENT DOCUMENTS

DE     3924345 A1 *  1/1991

(Continued)

OTHER PUBLICATIONS

Artz, E., Size Effects in Materials due to Microstructural and Dimensional Constraints: A Comparative Review, Acta Mater, 46, 5611-5626 (1998).

(Continued)

*Primary Examiner*—Hezron Williams
*Assistant Examiner*—Nathaniel Kolb
(74) *Attorney, Agent, or Firm*—Greer, Burns & Crain, Ltd.

(57) ABSTRACT

Methods and apparatus for testing a microscale or nanoscale sample. A testing stage comprises a frame having first and second laterally opposing ends and first and second side beams. At least one deformable force sensor beam is disposed near the first opposing end and extends laterally between the first and second side beams. A first longitudinal beam, having a free end, bisects the at least one force sensor beam, and a second longitudinal beam has a free end facing the free end of the first longitudinal beam to define a gap therebetween. A support structure comprises a plurality of laterally extending beams disposed such that the second longitudinal beam bisects the plurality of laterally extending beams. Each of a pair of slots disposed at each of the free ends of the first and second longitudinal beams comprises a tapered portion leading to a generally longitudinal portion aligned with the central longitudinal beam. The slots provide a seat for a dogbone-shaped sample.

6 Claims, 10 Drawing Sheets

FOREIGN PATENT DOCUMENTS

DE            4241045         5/1994

OTHER PUBLICATIONS

Badawi, K.F. et. al., Measuring thin film and multilayer elastic constants by coupling *in situ* tensile testing with x-ray diffraction, Appl. Phys. Lett., 80, 4705 (2002).

Bohm, J. et. al., Tensile testing of ultrathin polycrystalline films: A synchrotron-based technique, Rev. Sci. Instrum., 75, 110 (2004).

Bonetti, E. et al., The influence of Grain Size on the Mechanical Properties of Nanocrystalline Aluminum, Nanostructured Materials, vol. 9, pp. 611-614, 1997.

Chasiotis, I. et. al., A New Microtensile Tester for the Study of MEMS Materials with the Aid of Atomic Force Microscopy, Exp. Mech, 42, 51 (2002).

Espinosa, H.D. et. al., A methodology for determining mechanical properties of freestanding thin films and MEMS materials, J. Phys. Solids, 51, 47 (2003).

Espinosa, H. D. et al., Plasticity size effects in free-standing submicron polycrystalline FCC films subjected to pure tension, Journal of the Mechanics and Physics of Solids, vol. 52, pp. 667-689, 2004.

Espinosa, H. D. et al., An interpretation of size-scale plasticity in geometrically confined systems, Proceedings of the National Academy of Sciences, vol. 102, No. 47, pp. 16933-16938, 2005.

Flinn, P.A. et. al., Measurement and Interpretation of Stress in Aluminum-Based Metallization as a Function of Thermal History, IEEE Trans. Electron Devices, ED-34, 689 (1987).

Gutkin, M.Y. et. al., Theoretical Models of Plastic Deformation Processes in Nanocrystalline Materials, Rev. Adv. Mater. Sci., 2, 80 (2001).

Haque, M.A. et. al., In-situ Tensile Testing of Nano-scale Specimens in SEM and TEM, Experimental Mechanics, vol. 42, pp. 123-128 (2002).

Haque, M.A. et al., A Review of MEMS-Based Microscale and Nanoscale Tensile and Bending Testing, Experimental Mechanics, vol. 43, No. 3, pp. 248-255, 2003.

Haque, M.A. et. al., Mechanical behavior of 30-50 nm thick aluminum films under uniaxial tension, Scr. Mater., 47, 863 (2002).

Haque, M.A. et. al., Application of MEMS force sensors for in situ mechanical characterization of nano-scale thin films in SEM and TEM, Sensors and Actuators A, vol. 97-98, pp. 239-245 (2002).

Haque, M.A. et. al., Deformation mechanisms in free-standing nanoscale thin films: A quantitative *in situ* transmission electron microscope study, Proceedings of the National Academy of Sciences, vol. 101, No. 17, pp. 6335-6340 (2004).

Haque, M.A. et. al., Thermo-mechanical properties of nano-scale freestanding aluminum films, Thin Solid Films, 484, 364 (2005).

Hattar, K. et. al., In situ transmission electron microscopy observations of toughening mechanisms in ultra-fine grained columnar aluminum thin films, J. Mater. Res., 20, 1869 (2005).

Hugo, R. C. et al., In-situ TEM tensile testing of DC magnetron sputtered and pulsed laser deposited Ni thin films, Acta Materialia, vol. 51, pp. 1937-1943, 2003.

Jackson, K. M. et. al., Mechanical Properties of Epitaxial 3C Silicon Carbide Thin Films, J. Microelectromech. Syst., 14, 664 (2005).

Kraft, O. et. al., X-ray diffraction as a tool to study the mechanical behaviour of thin films, Mater. Sci. Eng., A 288, 209 (2000).

Legros, M. et al., Microsample tensile testing of nanocrystalline metals, Philosophical Magazine A, vol. 80, No. 4, pp. 1017-1026, 2000.

Neugebauer, C.A. et. al., Tensile Properties of Thin, Evaporated Gold Films, J. Appl. Phys., 31, 1096 (1960).

Renault, P.O. et. al., Damage mode tensile testing of thin gold films on polyimide substrates by X-ray diffraction and atomic force microscopy, Thin Solid Films, 424, 267 (2003).

Ruud, J.A., A new method for tensile testing of thin films, J. Mater Res., 8, 112, (1993).

Teer, D.G., et. al., The Formation of Low Friction Wear-Resistant Surfaces on Titanium by Ion Plating, Thin Solid Films, 45, 583 (2001).

Tsuchiya, T. et. al., Specimen Size Effect on Tensile Strength of Surface-Micromachined Polycrystalline Silicon Thin Films, J. Microelectromech. Syst., 7, 106 (1998).

Uchic, M.D. et al., A methodology to investigate size scale effects in crystalline plasticity using uniaxial compression testing, Materials Science & Engineering A, vol. 400-401, pp. 268-278, 2005.

Uchic, M.D. et al., 3D microstructural characterization of nickel superalloys via serial-sectioning using a dual beam FIB-SEM, Scripta Materialia, vol. 55, No. 1, pp. 23-28. 2006.

Xiang, Y. et. al., Plane-strain bulge test for thin films, J. Mater. Res., 20, 2360 (2005).

Yi, S. H. et al., Electroless Nickel Films: Properties and Fabricated Cavity Structure, Journal of Microelectromechanical Systems, vol. 11, No. 4, pp. 293-301, 2002.

Yu, D.Y.W., The yield strength of thin copper films on Kapton, J. Appl. Phys., 95, 2991 (2004).

Behr, R. et al., TEM Investigation of the Superdislocations and their Interaction with Particles in Dispersion Strengthened Intermetallics, Intermetallics, 7, pp. 423-436, 1999.

Brotzen, F.R., Mechanical Testing of Thin Films, International Materials Reviews, vol. 39, No. 1, pp. 24-45, 1994.

Chechenin, N.G. et al., Nanoindentation of Amorphous Aluminum Oxide Films III. The Influence of the Substrate on the Elastic Properties, Thin Solid Films, 304, pp. 70-77, 1997.

Gibeling, J.C. et al., Observations of Anelastic Backflow Following Stress Reductions During Creep of Pure Metals, Acta Materialia, vol. 29, pp. 1769-1784, 1981.

Greek, S. et al., Micromechanical Tensile Testing, Materials Research Society Symposium Proceedings, vol. 436, pp. 227-232, 1997.

Han, J. et al., *In situ* microtensile stage for elecromechanical characterization of nanoscale freestanding films, Review of Scientific Instruments, vol. 77, No. 4, pp. 45102-1-8, 2006.

Haque, M.A. et al., Microscale Materials Testing Using MEMS Actuators, Journal of Microelectromechancial Systems, vol. 10, No. 1, Mar. 2001, pp. 146-152.

Hoffman, R.W., Nanomechanics of Thin Films: Emphasis: Tensile Properties, Mater. Res. Soc. Symp. Proc., 130, 295 (1989).

Huang, H. et al., Tensile Testing of Free-Standing Cu, Ag and Al Thin Films and Ag/Cu Multilayers, Acta Materialia, vol. 48, No. 12, pp. 3261-3269, 2000.

Kang, Y.S. et al., Thickness Dependent Mechanical Behavior of Submicron Aluminum Films, Journal of Electronic Materials, vol. 26, No. 7, pp. 805-813, 1997.

Ké, T.S. et al., Structure of Cold-Worked Metals as Deduced from Anelastic Measurements, Symposium on Plastic Deformation of Crystalline Solids, Mellon Institute, Pittsburgh, pp. 185-192, 1950.

Nix, W.D. et. al., Mechanical Properties of Thin Films, Trans A, 20A, 2217 (1989).

Read, D.T., Piezo-Actuated Microtensile Test Apparatus, American Society for Testing and Materials, vol. 26, No. 3, pp. 255-259 (1998).

Robertson, I.M. et al., Application of In-Situ TEM Deformation Techniques to Observe how "Clean" and Doped Grain Boundaries Respond to Local Stress Concentrations, Ultramicroscopy, vol. 40, pp. 330-338, 1992.

Sanders, P.G. et al., Elastic and Tensile Behavior of Nanocrystalline Copper and Palladium, Acta Materialia, vol. 45, No. 10, pp. 4019-4025, 1997.

Spaepen, F. et al., Mechanical Properties of Thin Films & Multilayers, Current Opinion in Solid State and Materials Science, 1: 679-683, 1996.

Tang, W.C. et al., Laterally Driven Polysilicon Resonant Microstructures, Sensors and Actuators A, 20, pp. 25-32, 1989.

Yuan, B., Mechanical Testing of Polysilicon Thin Films with the ISDG, Exp. Mech., 21, 32 (1997).

\* cited by examiner

APPARATUS AND METHOD FOR MATERIAL TESTING OF MICROSCALE AND NANOSCALE SAMPLES

STATEMENT OF GOVERNMENT INTEREST

This invention was made with Government assistance under United States Air Force (USAF) Grant No. USAF 5212-STI-SC-0004. The Government has certain rights in the invention.

FIELD OF THE INVENTION

A field of the invention is material testing of microscale and nanoscale samples.

BACKGROUND OF THE INVENTION

As part of micro-electronic and micro-electromechanical systems (MEMS), microscale and nanoscale materials exhibit mechanical properties and deformation mechanisms that are different from their bulk counterparts. Accurately predicting material response requires understanding the fundamental mechanisms of material deformation and fracture occurrence in microscale and nanoscale. Material properties typically cannot be extrapolated from their respective bulk values, since material behavior often is not only different in microscale, but is also significantly affected by microstructure, sample size, and/or fabrication processes, and further is very sensitive to the influences of interfaces and adjoining materials. Changes in grain size and sample texture may lead to different responses even for the same materials. Some deformation mechanisms that are unimportant at bulk scale may become dominant as the sample's volume decreases and the relative surface area increases, such as in thin films. For example, samples made by gas deposition may exhibit different characteristics from those obtained by chemical clustering. As another example, samples fabricated by mechanical attrition of metal powders may behave differently than the ones that are segmented from bulk materials.

Experiments to determine mechanical behavior and deformation mechanism at macroscale have been largely successful. Yet, as the need for using smaller-scale materials has increased with the development of microelectronics and micro-sensors, it becomes increasingly important to assess the mechanism of deformation and failure of materials at microscale and nanoscale. However, due to the limited number of testing techniques for microscale and nanoscale samples, characterizing materials at these small scales has been a challenge, and much effort has been put into developing apparatuses and methods for testing.

Various material properties tests require tensile loading of a material sample (specimen). One popular testing method is the uniaxial tensile test. This test involves gripping a specimen at opposing ends, and producing tension in the specimen along a single axis while measuring the specimen's response. In the microscale or nanoscale, however, certain challenges arise when loading specimens, such as: gripping of the specimen; aligning of the specimen in the direction of the force (to minimize likelihood of invalidation of the test caused by flexural stress on the specimen and resultant premature failure); and generating small forces (e.g., on the order of micro-Newtons) with high resolutions.

These challenges can be addressed by using a substrate layer that is usually very compliant and with known material properties along with the actual specimen to be tested. However, introduction of the substrate complicates the experimental analysis because the microscale material properties of the substrate itself may not be known accurately, and because the interface with the substrate may influence the mechanical behavior of the specimen.

For example, a method of fabricating freestanding aluminum films includes evaporating metal film on a glass slide covered with a water-soluble layer, releasing the thin film from the glass slide by immersing it in water, and gluing the film to grips of a nano-tensilometer with epoxy. However, problems of mounting the specimen and premature specimen failure invalidate a significant number of tests using this method, and experimental results from the tests have shown significant variation in measured elastic modulus and ultimate tensile strength.

Another prior fabrication technique includes sputtering metal film on glass slides and releasing the films by peeling the films off from a substrate. A motor-driven micrometer is used to produce elongation in the films, and a load cell is used to read the stress. Laser spots diffracted from the gratings on the specimen surface determine the strain with 0.002% resolution.

Yet another known method provides a piezo-actuated tensile testing apparatus using Ti—Cu—Ti multilayer films with a length of 700 microns, a width of 200 microns, and a total thickness of 1.2 μm patterned on wafers by lithography. The films are then released from the substrate by wet etching of the substrate. Such a tensile testing apparatus has been known to provide force and displacement resolutions of about 200 μN and 20 nm, respectively. Still another testing method uses piezoelectric actuators for displacement with a load cell, a laser interferometer, and a strain gauge-optical encoder assembly to measure force and displacement.

A more recent material testing method is disclosed in U.S. Pat. No. 6,817,255, issued Nov. 16, 2004 (the '255 Patent) to Hague and Saif, which is incorporated herein by reference. The '255 Patent discloses an apparatus and method for uniaxial tensile testing of a thin film material. This apparatus allows quantitative study of thin metal films down to very small thicknesses. The compact size and displacement-based measurement of example devices in the '255 Patent allows one to conduct in-situ quantitative and qualitative tensile testing in environments such as a transmission electron microscope (TEM) and a scanning electron microscope (SEM).

An example apparatus disclosed in the '255 Patent includes a testing stage (e.g., a compact MEMS-based chip) that includes a co-fabricated thin film specimen to be tested, held by at least one force sensor beam at a first longitudinal end and by a support structure at a second longitudinal end. An example support structure includes a longitudinal beam connected to the second longitudinal end and aligned with the tensile axis of the specimen, and a plurality of lateral support beams. The support beams reduce flexing of the specimen resulting from misalignment of the pulling direction with the tensile axis of the specimen, thus ensuring that a sample is subjected to uniaxial tension. Preferred embodiments of the chip include a pair of structural springs fabricated for maintaining structural integrity between the first and second ends of the chip and for addressing misalignment. Markers (e.g., displacement gauges) may be provided for measuring displacement of longitudinal ends of the specimen and deflection of the force sensor beam.

To test the thin film sample, the ends of the stage are separated (e.g., pulled) from one another by an actuator, such as a piezo actuator in SEM or a motor in TEM, which produces a tensile load on the sample. Measured displacement is used to determine material properties of the thin film specimen. For example, the force on the sample is determined from the displacement of the force sensor beams and the spring constant of the force sensor beam(s). The spring constant may be determined mathematically given dimensions and properties of the force sensor beams and/or by calibration, such as by using a nanoindenter. Sample stretching may be measured, for example, by measuring displacement of the force sensor beams and the support structure.

Another testing stage for testing thin film samples is disclosed in Han, J. and Saif, M. T. A., "In Situ microtensile stage for electromechanical characterization of nanoscale freestanding films", Review of Scientific Instruments, Vol. 77, No. 4, pp. 45102-1-8, 2006 ("Han and Saif"), which is incorporated herein by reference. This testing stage allows more accurate calibration prior to testing (e.g., without nanoindentation after cleaving the stage) and electrical resistivity measurement of the sample in addition to stress-strain response.

An example embodiment disclosed in Han and Saif uses a testing stage co-fabricated with a thin film specimen, as with the '255 Patent. The specimen is disposed between a support structure with a longitudinal beam axially aligned with a tensile axis and a plurality of lateral beams at one end, and by one or more deformable, lateral force sensor beams with a bisecting longitudinal beam at the opposite end. To protect the metal thin film sample from possible premature failure during fabrication of the testing stage, a protecting beam is provided. The protecting beam extends parallel to the co-fabricated sample and connects the support structure to the longitudinal beam bisecting the force sensor beams.

After fabricating the sample, the protecting beam is cut using focused ion beam (FIB), to provide a displacement gauge. A laterally extending beam disposed between the support structure and the force sensor beams provides a reference displacement gauge. Tensile testing is performed similarly to that described in the '255 Patent. The displacement gauges measure displacement of the sample and the force sensor beams, and are sufficiently near the sample to allow simultaneous observation of the sample stress-strain and the displacement gauges in an observation chamber.

For calibrating the force sensor beams, Han and Saif discloses using two silicon calibrators. Both calibrators are silicon chips including an opening for connecting to a moving stage, a guide spring for improving alignment, and a leaf spring for calibration. A first calibrator, known as a master calibrator, is glued to a larger substrate that allows calibration of the first calibrator's leaf spring by a nanoindenter. This leaf spring is then urged against the second calibrator's leaf spring to calibrate it. An opening of the testing stage adjacent to the force sensor beams receives the second calibrator, and guides in the second calibrator mate with guide fits in the opening to align the calibrator within the testing stage. The second calibrator's leaf spring is urged against the force sensor beams to calibrate the force sensor beams.

In addition to tensile testing, the testing stage disclosed in Han and Saif may be used for electrical resistive testing of a sample. A metal film is deposited over the (silicon) testing stage substrate during fabrication, and metal isolations, formed by removing metal and oxide, are patterned in the testing stage to provide isolated electrodes coupling the thin film specimen to connection points. Han and Saif disclose providing a four-point resistance measurement using the isolated electrodes.

However, both the testing stage disclosed in the '255 Patent and the testing stage disclosed in Han and Saif use a co-fabricated thin film sample. This can limit the types of samples, and sample materials, that are available for testing.

Further, both testing stages allow tensile testing, but not other types of material testing, such as compressive testing.

SUMMARY OF THE INVENTION

Embodiments of the present invention provide, among other things, methods and apparatus for testing a microscale or nanoscale sample. A testing stage comprises a frame having first and second opposing ends and first and second side beams. At least one deformable force sensor beam is disposed near the first opposing end and extends laterally across the frame between the first and second side beams. A first longitudinal beam, having a free end, bisects the at least one force sensor beam, and a second longitudinal beam has a free end facing the free end of the first longitudinal beam to define a gap therebetween. A support structure near the second opposing end comprises a plurality of laterally extending beams disposed such that the second longitudinal beam bisects the plurality of laterally extending beams.

A pair of slots is disposed at each of the free ends of the first and second longitudinal beams. Each of the slots comprises a tapered portion leading to a generally longitudinal portion aligned with the central longitudinal beam. The pair of slots together provide a seat for a dogbone-shaped sample.

BRIEF DESCRIPTION OF THE DRAWINGS

FIGS. 12A-12E show stages of the single crystal Ni superalloy sample of FIG. 11 during uniaxial testing, where.

DETAILED DESCRIPTION

Embodiments of the present invention provide, among other things, methods and apparatuses for material testing of a nanoscale or microscale sample (specimen), allowing testing of the sample in situ within a number of testing environments, including but not limited to a chamber such as a scanning electron microscope (SEM) or transmission electron microscope (TEM) chamber. An example testing stage can be provided using microfabrication techniques so that the chip is small enough to be placed within a chamber without modification, allowing both qualitative and quantitative in-situ experimentation of the sample on a microscale or nanoscale. The testing stage may be used for a variety of tests requiring tensile or compressive loading of a specimen, such as testing of uniaxial tension or compression, tension-tension fatigue, electrical resistance (including resistance under stress), and low and high temperature creep, among others.

Particular embodiments of the present invention provide a MEMS-based testing stage, which allows both uniaxial tensile and compressive testing of externally fabricated microscale samples for quantitative study of their mechanical behavior and simultaneous observation of their microstructural and topological evolution in situ. Generally, example testing stages according to embodiments of the present invention include a frame having first and second longitudinally opposed ends and laterally opposed sides. A first longitudinal beam near the first end is connected to at least one force sensor beam, which runs laterally between the sides. The first longitudinal beam includes a free end. A second longitudinal beam coaxial with the first longitudinal beam also has a free end and is disposed so that a gap is provided between the free ends of the first and second longitudinal beams. A support structure includes a plurality of laterally extending beams disposed near the second end. The second longitudinal beam bisects the laterally extending beams.

The free ends of the first and second longitudinal beams each include a slot, and these two slots provide a seat for part of an externally fabricated, dogbone shaped sample. The slots include a tapered portion leading to a generally longitudinal portion extending to the edge of the free ends. When the dogbone shaped sample is placed within the slots, the sample spans the gap between the free ends, and the slots serve as a grip for the ends of the sample.

The force sensor beams may be calibrated by a calibrator that is inserted into an opening in the testing stage. An exemplary calibrator is a chip including a leaf spring that is pre-calibrated using a nanoindenter, and then inserted into the opening. The leaf spring is urged against the force sensor beams to calibrate the force sensor beams.

To test a microscale or nanoscale sample, the sample is inserted into the slots to span and connect the first and second longitudinal beams. The first and second ends of the testing stage are moved relative to one another, such as away from one another for tensile testing, and toward one another for compressive testing. In an example embodiment, movement is provided by a moving stage (loading stage) having portions that are inserted into openings in the first and second ends of the frame. Example moving stages include both a coarse, spring-loaded actuator and a fine piezo actuator. The support structure, preferably in combination with one or more U-shaped springs and the dogbone shape of the sample, maintains uniaxial movement during either tensile or compressive testing.

During relative movement of the first and second ends, one or more displacement gauges are used to measure stretching of the specimen and the force on the force sensor beams. Preferably, the displacement gauges are provided near the sample, such as by the free ends of the first and second longitudinal beams in combination with a laterally-extending center gauge, so that the displacement can be observed simultaneously with deformation of the sample. A metal film may be provided on the testing stage and separated by selectively placed metal isolators to define resistors for measuring electrical resistance of the sample, including electrical resistance under sample stress and at room temperature.

Preferred embodiments allow testing of any of various types of materials, including organic, inorganic, or a combination of materials. Sample materials include, but are not limited to, metals (including single-crystal or polycrystal), dielectrics, biological materials, and/or multi-layer composites, that can be fabricated in a suitable shape to fit within a sample slot in the testing stage. Embodiments of the invention are particularly useful for probing microscale or nanoscale material behavior, where the deformation characteristics are expected to deviate significantly from bulk values. Preferred samples are made into a dog-bone shape to ensure uniaxial tension or compression. Because the samples are fabricated separately, a greater variety of samples are possible for material testing than that available under certain previous methods. Further, separately fabricated samples allow the testing stage to be reusable.

Preferred embodiments will now be discussed with respect to the drawings. The drawings include schematic figures that may not be to scale, which will be fully understood by skilled artisans with reference to the accompanying description. Features may be exaggerated for purposes of illustration. From the preferred embodiments, artisans will recognize additional features and broader aspects of the invention.

Figure 1:
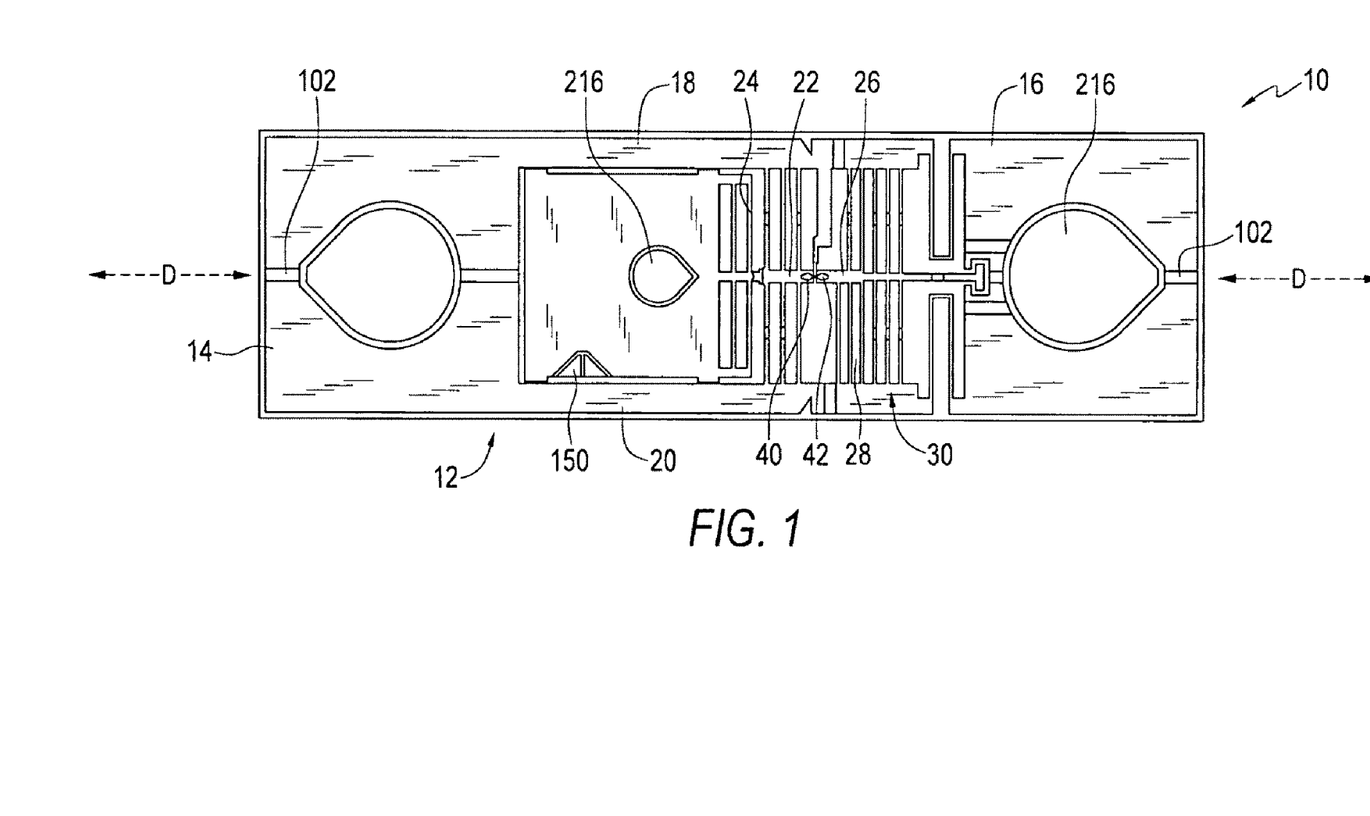
FIG. 1 shows a testing stage according to an embodiment of the present invention.
Figure 2:
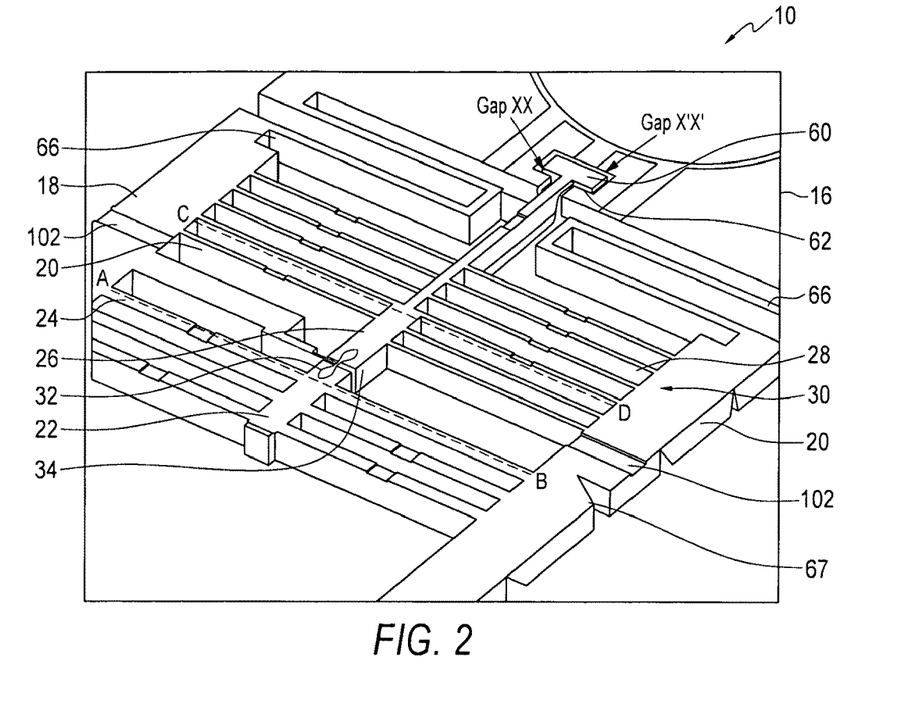
FIG. 2 shows an enlarged portion of the testing stage of FIG. 1, with a calibrator removed.

FIGS. 1 and 2 show an example micromechanical testing stage 10 according to an embodiment of the present invention. In an example embodiment, the testing stage 10 includes silicon substrate material fabricated using microfabrication methods. Generally, the testing stage 10 includes a generally rectangular frame 12 having a first opposing end 14 and a second opposing end 16. A pair of laterally opposed side beams 18, 20 extend longitudinally between the first opposing end 14 and the second opposing end 16. The testing stage 10 may be of various dimensions. If a thin wafer (e.g., silicon) is used, a relatively small testing stage can be provided.

During testing, the first end 14 is moved relative to the second end 16 (for example, by a moving stage such as a straining stage). For tensile testing, the first end 14 and the second end 16 are moved away from one another along a displacement direction D, while for compressive testing, the first end and the second end are moved toward one another along the displacement direction. Either the first end 14 or the second end 16 may be a fixed end, while the other end is moved. Alternatively, both ends 14, 16 may be moved while loading.

For supporting a sample (specimen) to be tested, the testing stage 10 includes a first longitudinal beam 22 that is substantially laterally centered within the frame and coaxial with the displacement direction D. The first longitudinal beam 22 bisects one or more, and preferably several, deformable force sensor beams 24. These force sensor beams 24 extend laterally between the first and second side beams 18, 20. As shown in FIG. 2, the force sensor beams extend along a lateral line such as line AB. The force sensor beams 24 provide support to the first longitudinal beam 22, and they are configured to deflect in response to a tensile or compressive stress on the sample. Using a plurality of force sensor beams 24 in the testing stage 10 allows a larger range of spring constants when testing the sample. For example, if the sample to be used is soft, one or more of the force sensor beams 24 may by cut (such as by focused ion beam (FIB)) to lower the beam stiffness and attain higher force resolution.

The testing stage 10 also includes a second laterally centered longitudinal beam 26, also coaxial with the displacement direction D, which bisects a plurality of laterally extending support beams 28. These generally rectangular beams 28, which extend laterally between the first and second side beams 18, 20 (such as along line CD in FIG. 2), provide a support structure 30 for supporting the second longitudinal beam 26, and help to reduce misalignment during loading. While five support beams 28 are shown in FIGS. 1-2, it will be appreciated that less than or more than five support beams are possible. Other configurations for the support beams are possible. Thus, the support structure 30 is not intended to be limited to the configuration shown. It is preferred, however, that a plurality of support beams 28 be used.

The first and second longitudinal beams 22, 26 are coaxially disposed so that free ends 32, 34 of the beams face one another, the edges of which are separated by a gap 36. These free ends 32, 34 include generally symmetrical sample slots 40, 42, which support ends of a sample to be tested (see also FIGS. 3 and 4) and provide sample grips. During testing, an externally fabricated sample 44 is placed within the testing stage 10 so that first and second ends 46, 48 of the sample are seated within the sample slots 40, 42 at the free ends 32, 34. The sample 44 is partially suspended, spanning the gap 36 between the first and second longitudinal beams 22, 26 to connect the beams. An example length for the sample 44 is between one-half micron and 20 microns.

Figure 3:
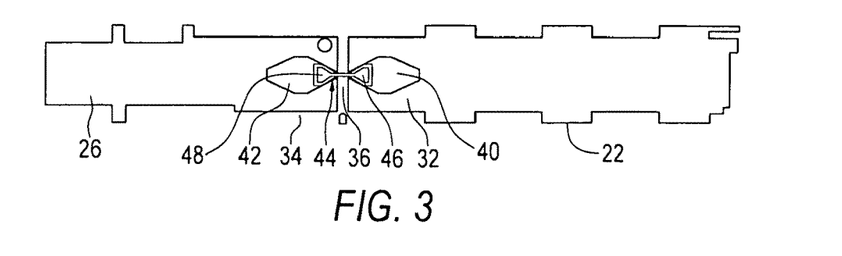
FIG. 3 shows a sample slot for the testing stage of FIG. 2, created by focused ion beam (FIB) within the sample slot shown in FIG. 2.
Figure 4:
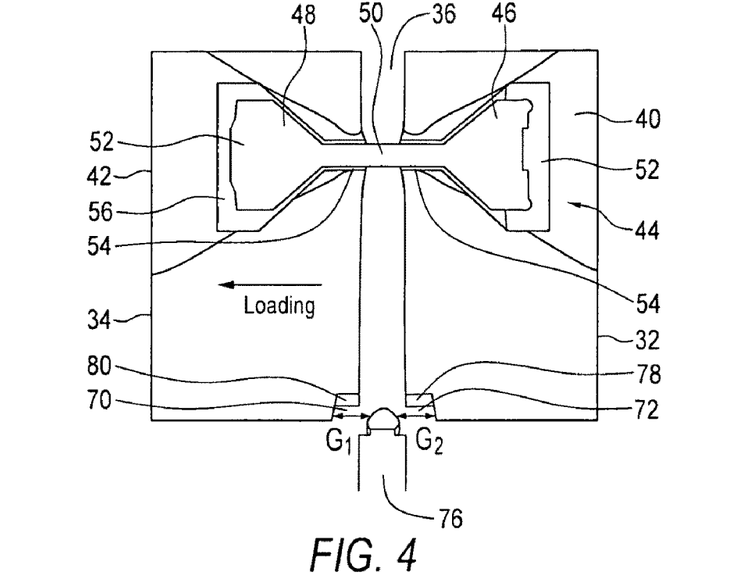
FIG. 4 shows a sample placed into the sample slot of FIG. 3.

The sample 44, made separately from the testing stage, preferably is formed into a dog-bone shape, and the sample slots 40, 44 in the free ends 32, 34 are similarly patterned in complementary parts of a dog-bone shape to receive the sample. Thus, the sample 44 includes a pair of enlarged, longitudinally opposed ends 46, 48 having at least a portion tapering inwardly to a more narrow longitudinal portion 50 extending therebetween. Similarly, the sample slots 40, 42 each include a laterally enlarged portion 52 that tapers inwardly to a narrower, longitudinal portion 54. The dogbone shape for the sample slots 40, 42 in combination, and for the sample 44, helps maintain a uniaxial load on the sample during testing. The longitudinal portions 54 of the sample slots 40, 42 are coaxial with the displacement direction D.

The taper in the sample slots 40, 42 and in the sample 44 is preferably at an angle of about 25° with respect to the displacement direction (loading axis) D. Therefore, the sample 44 can self-align with the displacement direction D during loading. While the sample slots 40, 42 shown in FIG. 2 are formed by patterning and Si etching, different shapes of slots can also be created by focused ion beam (FIB) on the original slot. For example, a more refined slot 56 may be made by FIB on the original slots 40, 42 for tensile testing of a Ni super alloy sample, as shown in FIGS. 3 and 4.

Because the sample 44 in embodiments of the present invention is externally fabricated and then placed into the sample slots 40, 42, a large range of materials are available for the sample. For example, the sample 44 may be made of metal, including single crystal or polycrystal, biological material, organic or inorganic material, a composite structure, etc. Further, because the samples 44 are freely insertable and removable, the testing stage 10 may be reused after material testing.

The support structure 30 supporting the second longitudinal beam 26 transmits the displacement between the first and second ends 14, 16 of the testing stage 10 to the sample 44 during testing via the second longitudinal beam. The support beams 24 correct load misalignment between the displacement direction D and the load axis of the sample 44. Similarly, the force sensor beams 24 sense a force transmitted to the sample 44 via the first longitudinal beam 22.

For preventing premature loading of the sample 44 within the testing stage 10, the second longitudinal beam 26 preferably terminates beyond the support structure 30 in a cantilevered support end 60 opposite the free end 34. The cantilevered support end 60 extends laterally from the center of the second longitudinal beam 26, forming a symmetrical, generally T-shaped end. An opening 62 is formed in the second end 16 to accommodate the cantilevered end 60, and this opening is slightly larger than the cantilevered end to provide small gaps XX and X'X' on longitudinally opposed sides of the cantilevered end. As shown in FIG. 1, gap XX is longitudinally closer to the sample 44, and gap X'X' is longitudinally farther from the sample. During tensile loading, the testing stage 10 has to be pulled to first close the gap XX before straining the sample 44. Similarly, during compressive loading, the testing stage 10 has to be pushed to first close the gap X'X' before imparting a compressive load on the sample 44.

To further correct misalignment between the sample 44 and the loading axis D, and for providing structural integrity to the testing stage 10, a pair of springs 66 such as U-shaped springs is provided at each lateral side near the side beams 18, 20 or elsewhere on the testing stage. These springs 66 deform when the first end 14 and the second end 16 are pulled apart during relative movement (e.g., during actuation of the testing stage 10), and thus substantially prevent the side beams 18, 20 between the springs and first end 14 from deforming. This also facilitates transmission of the displacement between the ends 14, 16 along the second longitudinal beam 26 to the sample 44. Cutouts 67 may be provided within the side beams 18, 20 for further improving structural integrity.

The inward edges at the facing free ends 32, 34 of the first and second longitudinal beams 22, 26 provide displacement gauges 70, 72 for measuring stress of the force sensor beams 24 and displacement of the ends 46, 48 of the sample 44. Referring also to FIG. 4, a center gauge 76 is provided by an Si beam that extends laterally from the side beam 18 toward the edges, and preferably is longitudinally centered between the gauges 70, 72, functioning as a reference. Cutouts 78, 80 at the edges may be provided to further define the displacement gauges (e.g., to provide a larger range of measurement without interfering with the sample 44). In an example embodiment, a gap $G_1$ is defined between the first gauge 70 and the center gauge 76, and a gap $G_2$ is defined between the second gauge 72 and the center gauge.

To apply load on the sample 44, the testing stage 10 is actuated so that initially the gap 36, XX or X'X', is closed for tensile or compression testing, respectively. Further actuation applies load on the sample 44, and the gaps, $G_1$ and $G_2$, change. The change in $G_2$ gives the deflection of the force sensing beams 24, which in turn is used to calculate the force on the sample 44 by multiplying it with the stiffness of the force sensing beams. Subtracting the change in $G_2$ from that in $G_1$ gives the deformation and hence the strain of the sample 44.

It will be appreciated that additional or alternative displacement gauges (e.g., markers) may be provided on the testing stage 10 at different locations to measure the displacement in the sample 44 and the force on the sample. However, locating the displacement gauges 70, 72, 76 near the sample 44 allows the displacement gauges to be read simultaneously with observation of the sample. This may be especially useful during in situ monitoring and testing, such as within a TEM or SEM chamber, to enable simultaneous study of the sample's quantitative response as well as its microstructural and topological evolution during deformation.

An example fabrication process for making the testing stage 10 includes two patterning steps and two Si etching steps, as shown in FIGS. 5A-5F. Though Si is shown as an example substrate material, wafers of other material that can be suitably patterned, such as by microfabrication techniques, may be used for the substrate material.

Figure 5:
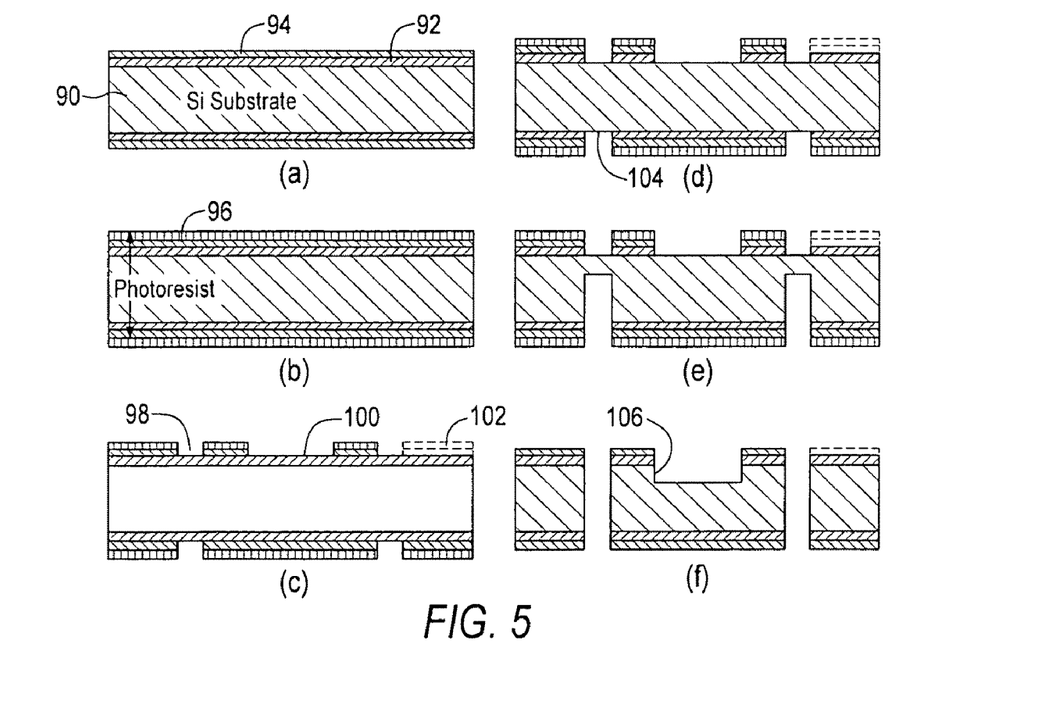
FIG. 5 shows steps in an exemplary fabrication process for a testing stage, according to an embodiment of the present invention.

Particularly, as shown in FIG. 5A, a 4" 150 μm thick Si wafer 90 is thermally oxidized at 1100° C. in oxygen environment for about an hour to obtain about 150 nm thick $SiO_2$ 92. A 50 nm thick metal layer 94, such as an Al layer, is sputter-deposited on both sides of an Si substrate (wafer). The Al layer on the front side of the wafer is used to create electrical paths for resistivity measurement, and the layer on the back side is used to enhance adhesion between the substrate and photoresist, such as AZ5214 positive photoresist. Both sides of the wafer are then coated by the photoresist 96 (FIG. 5B) and patterned by optical lithography. Preferably, a pattern 98 on the front of the wafer is a mirror image of that on the bottom except that the top has a dog-bone-shaped pattern 100 for the sample slot (FIG. 5C). This generally symmetrical pattern 98 in example embodiments allows the number of patterning and etching steps to be minimized.

Small openings 102 on the top Al layer are formed as electrical isolations, which allow current flow only through prescribed paths of the metal film 94. This defines a plurality of resistors within the metal film coupling the sample slot 40, 42 (thus coupling the inserted sample) to contacts defined by the Al layer 94. In a preferred embodiment, the resistors defined by the electrical isolators provide 4-point resistivity measurement of the sample. More particularly, a first resistive path is defined from the first longitudinal beam 22 through the side beam 18 and to the first opposing end 14, a second resistive path is defined from the first longitudinal beam through the side beam 20 and to the first opposing end, a third resistive path is defined from the second longitudinal beam 26 through the side beam 18 (and the U-spring 66) and to the second opposing end 16, and a fourth resistive path is defined from the second longitudinal beam through the side beam 20 (and the U-spring 66) and to the second opposing end. The first and third resistive paths, and the second and fourth resistive paths, are electrically coupled via the sample 44.

An example circuit diagram showing this four-point resistive measurement is disclosed in Han and Saif. This four-point resistive measurement eliminates any contribution of contact resistances in the measurement of the sample's resistance. In an example resistivity testing method, the current through the sample, e.g., through the first and third resistive path, is prescribed and the voltage across the sample, e.g., across the second and fourth resistive path, is measured. The ratio of the voltage measured over the current supplied gives the resistance of the metal sample.

Referring now to FIGS. 5D-5F, the photoresist pattern is transferred to the Al and $SiO_2$ layers 94, 92 by liquid etching and reactive ion etching (RIE) respectively, exposing Si areas 104 (FIG. 5D). These areas are etched (FIG. 5E) in an inductively coupled plasma-deep reactive ion etching (ICP DRIE) chamber from the back side until there is about 10 to 20 μm (or a different amount depending on how deep a sample slot needs to be) of Si left. A shallow Si etching 106 is conducted from the front side (FIG. 5F) to remove this remaining Si and to create a dogbone-shaped sample slot. Finally, the photoresist remainder 96 on the top and bottom is removed by $O_2$ plasma. Due to the small size of the center gauge area 76, the etch rate here from the bottom is slower than other larger open areas, resulting in thicker remainder of Si. After completion of Si etching, FIB cutting or additional Si etching may be used to separate the center gauge from the adjacent two sample grips at the edges of the free ends. The last dry Si etching step determines the depth of the sample slot. FIB cutting may also be used to make a differently-shaped or more refined sample slot on the Si-etched sample slot, though this is not required.

Figure 6:
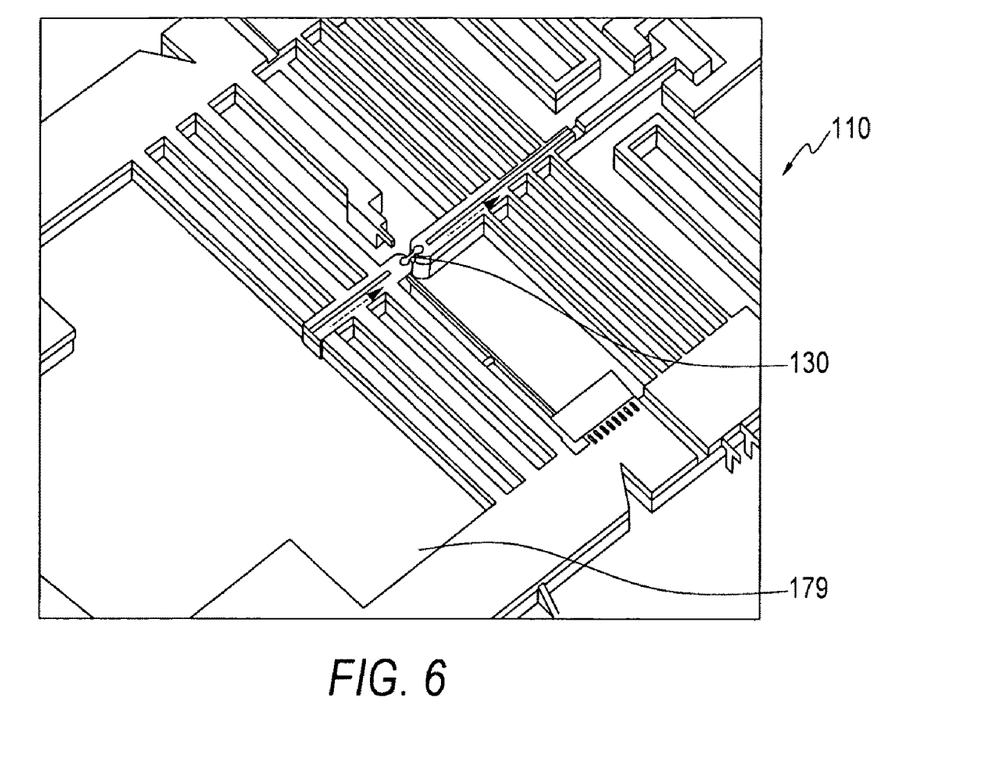
FIG. 6 shows an alternative testing stage, according to another embodiment of the present invention.
Figure 7:
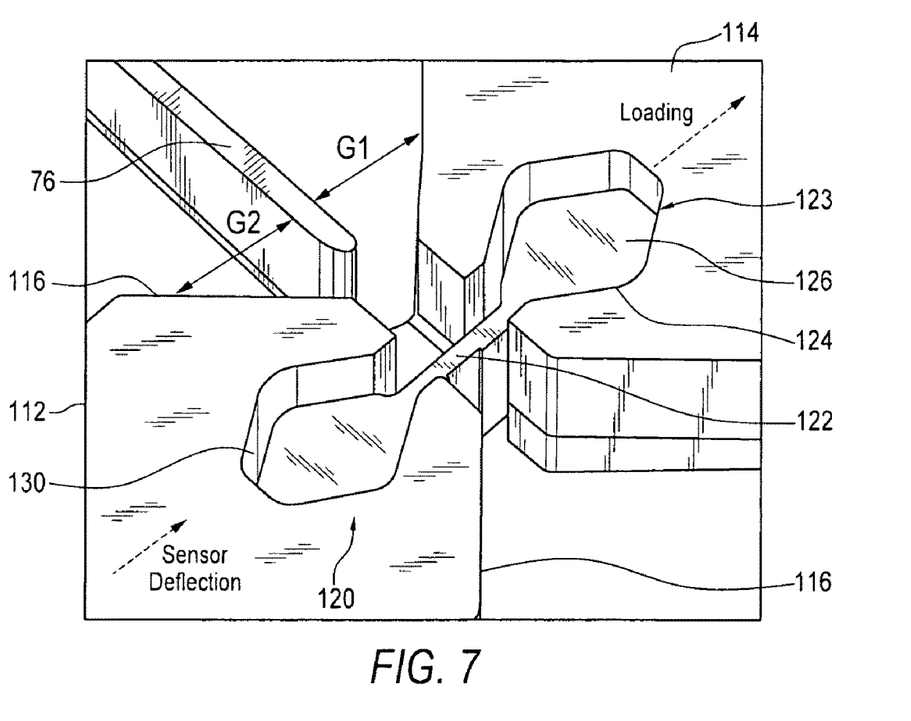
FIG. 7 shows a sample in a sample slot for the testing stage of FIG. 6, and displacement gauges.

For example, FIGS. 6 and 7 show an alternative testing stage 110 according to another embodiment of the present invention. Generally, the testing stage 110 is similar to the testing stage 10 shown in FIGS. 1-4, except for the configuration of the free ends of the first and second longitudinal beams, and the configuration of the sample slots. Particularly, as best seen in FIG. 7, free ends 112, 114 of the first and second longitudinal beams 22, 26, respectively, include symmetrical tapered edges 116 on either lateral side. These tapered edges 116 provide additional space for the reference gauge 76 extending laterally from the side beam 18. Gaps $G_1$ and $G_2$ are accordingly defined between sides of the reference gauge 76 and one or more locations along the tapered edges 116. This helps make the gauges 76, 116 closer to a sample than the gauges 70, 72, 76 in the testing stage 10, providing higher measurement resolution (e.g., three times higher).

Additionally, a sample 120 includes a center longitudinal portion 122 as with the longitudinal portion 50 of the sample 44, but further includes ends 123 having symmetrical inward tapers 124 and outward tapers 126. The tapers 124, 126 define a substantially rhombus-shaped ends, but with edged vertices. By contrast, the ends of the sample 44 preferably have a generally triangular shape. A well defined sample slot 130 in the free ends 112, 114 is shaped to receive the sample 120, and preferably is formed using microfabrication techniques, without FIB treatment (though FIB treatment may be used). The tapers 124, 126 help maintain a uniaxial load for both tension and compression.

Figure 8:
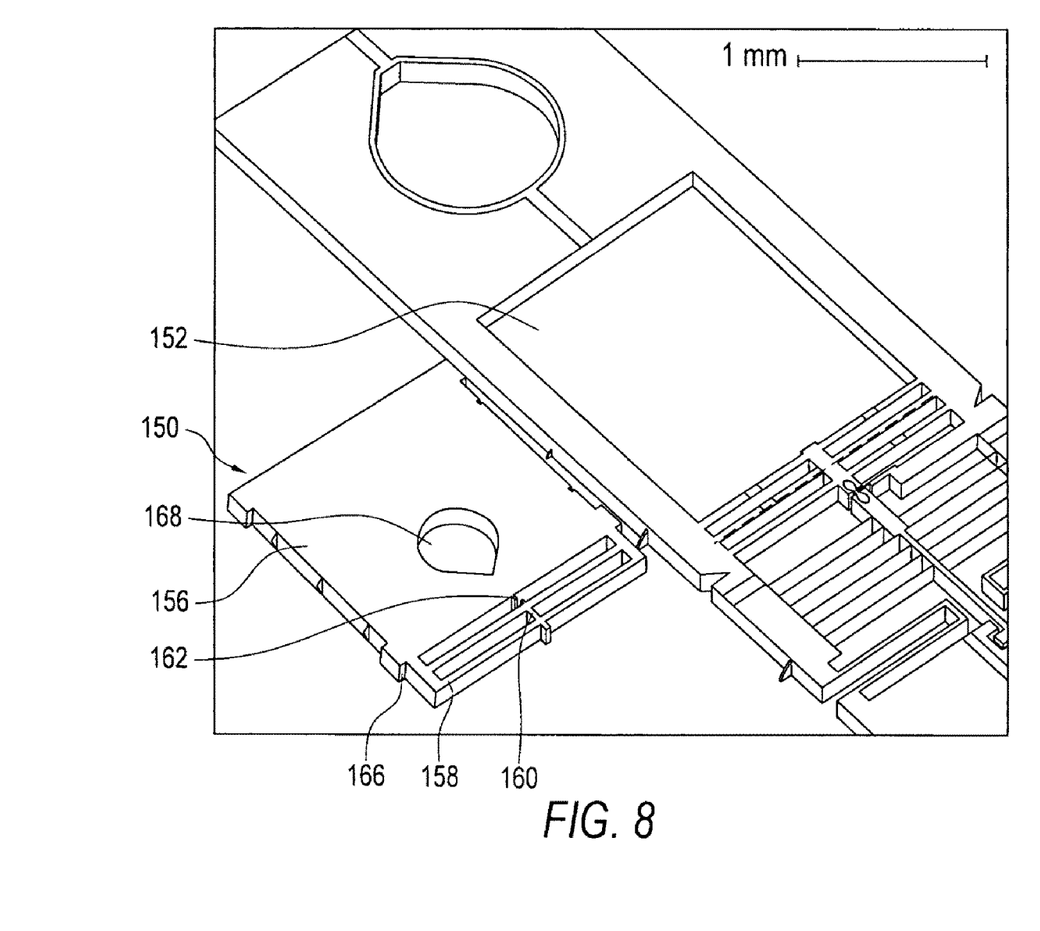
FIG. 8 shows a calibrator according to an embodiment of the present invention, before placement into an opening in the testing stage of FIG. 1.

As stated above, the measured change in $G_2$ gives the deflection of the force sensing beams 24, which is used to calculate the force on the sample 44 by multiplying it with the stiffness of the force sensing beams. To determine the stiffness (e.g., spring constant) of the force sensing beams 24, a formula may be used considering the material and dimensions of the force sensor beams, such as the formula as disclosed in the '255 Patent. Alternatively, the force sensing beams 24 may be calibrated using a calibrator. Referring to FIGS. 1 and 8, a calibrator 150 is provided that is insertable into an opening 152 in the testing stage 10 near the first opposing end 14 of the frame 12. The opening 152 is adjacent to the force sensing beams 24.

The example calibrator 150, which preferably is microfabricated from a silicon substrate material, has a frame 156 and two leaf springs 158 in series at an end of the frame. The leaf springs 158 are calibrated by a nanoindenter. A horizontal beam 160 bisects the leaf springs and terminates at one end in a gauge. A second horizontal beam 162 extends from the frame 156, facing the horizontal beam 160 and providing a reference gauge separated from the horizontal beam by a gap.

One or more guides, such as fingers 166, are disposed about an outer edge of the calibrator 150 for gripping an inner surface of the opening 152 and/or mating with guide slots in the opening. The fingers 166 help retain the calibrator 150 within the testing stage 10, and limit rotation of the calibrator, thus limiting misalignment when the calibrator is actuated. A generally teardrop-shaped loading hole 168 is provided within the calibrator 150 for insertion of a pillar from a moving stage. The calibrator frame may have different shapes. For example, an alternative calibrator has a generally T-shaped frame for inserting into a T-shaped opening 179, as shown in FIG. 6. The T-shaped calibrator and opening helps reduce misalignment during calibration. Additionally, the additional material provided for the frame of the testing stage 110 improves the structural integrity of the testing stage.

Figure 9A:
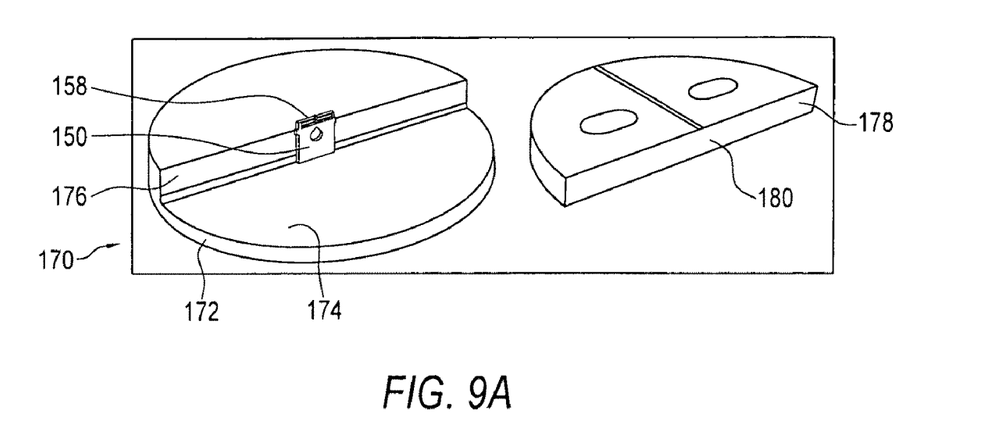
FIG. 9A shows a nanoindentation stage for calibrating the calibrator shown in FIG. 8.
Figure 9B:
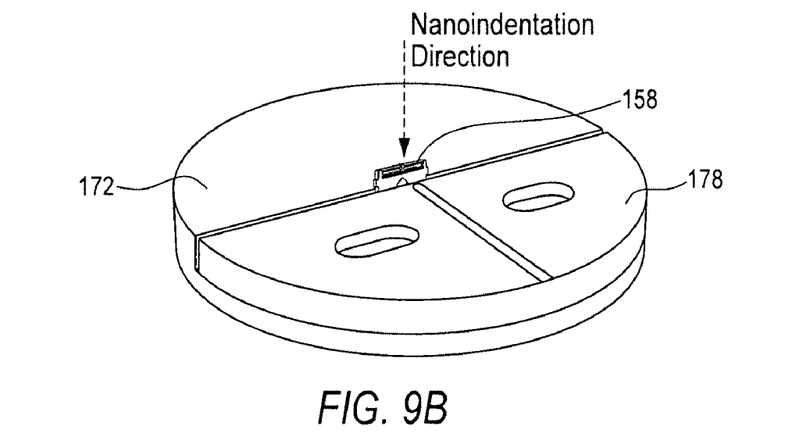
FIG. 9B shows a calibrator positioned in the nanoindentation stage of FIG. 9A prior to calibration.

Compared to the calibration technique disclosed in Han and Saif, exemplary calibration according to embodiments of the present invention uses a single calibrator. Using a single Si calibrator reduces calibration steps, in turn minimizing measurement error. This is made possible by providing a calibration stage 170 (FIGS. 9A-9B) that allows the calibrator to be removably placed within the calibration stage. Particularly, a base 172, which, for example, may be made of a machined metal, includes a horizontal surface 174 providing a calibration platform and a vertical surface 176 extending normal to the horizontal surface. The platform 174 allows the calibrator 150 to be placed upright against the vertical surface 176 with its leaf spring 158 facing up. A removable cover 178, including a vertical surface 180, is removably placed over the horizontal surface 174 such that the vertical surface 180 of the cover 178 and the vertical surface 176 of the base 172 sandwich the calibrator 150 therebetween, effectively clamping the calibrator for nanoindentation of the leaf springs 158. In the example calibration stage 170 shown in FIGS. 9A-9B, friction between the base 172 and cover 178 is sufficient to keep the calibrator clamped. However, it is also contemplated that clamps, fasteners, etc. may be used to retain the cover 178 in position to prevent undesirable movement of the calibrator 150 during nanoindentation, while allowing removal of the calibrator after calibration.

In an exemplary calibration method, after nanoindentation, the calibrator 150 is placed in the opening 152 inside the testing stage 10 to calibrate the force sensing beams 24, as shown in FIG. 1. An example method for measuring deflections and calculating spring constants is substantially the same as that disclosed in Han and Saif, except that a second calibrator is not required. Particularly, the calibrator 150 and the stage 10 are pushed toward each other, and the relative deflections from the leaf springs 158 of the calibrator and the force sensing beams 24 of the testing stage are measured from the change in the gaps of the respective gauges. The force sensing beams 24 and the leaf spring 158 are freestanding during calibration to avoid friction with a substrate. Preferably, the maximum possible misalignment between the calibrator 150 and the testing stage 10 is less than 1°, restricting the possible error in measuring the deflection of the leaf springs 158 down to less than 0.02%.

Figure 10:
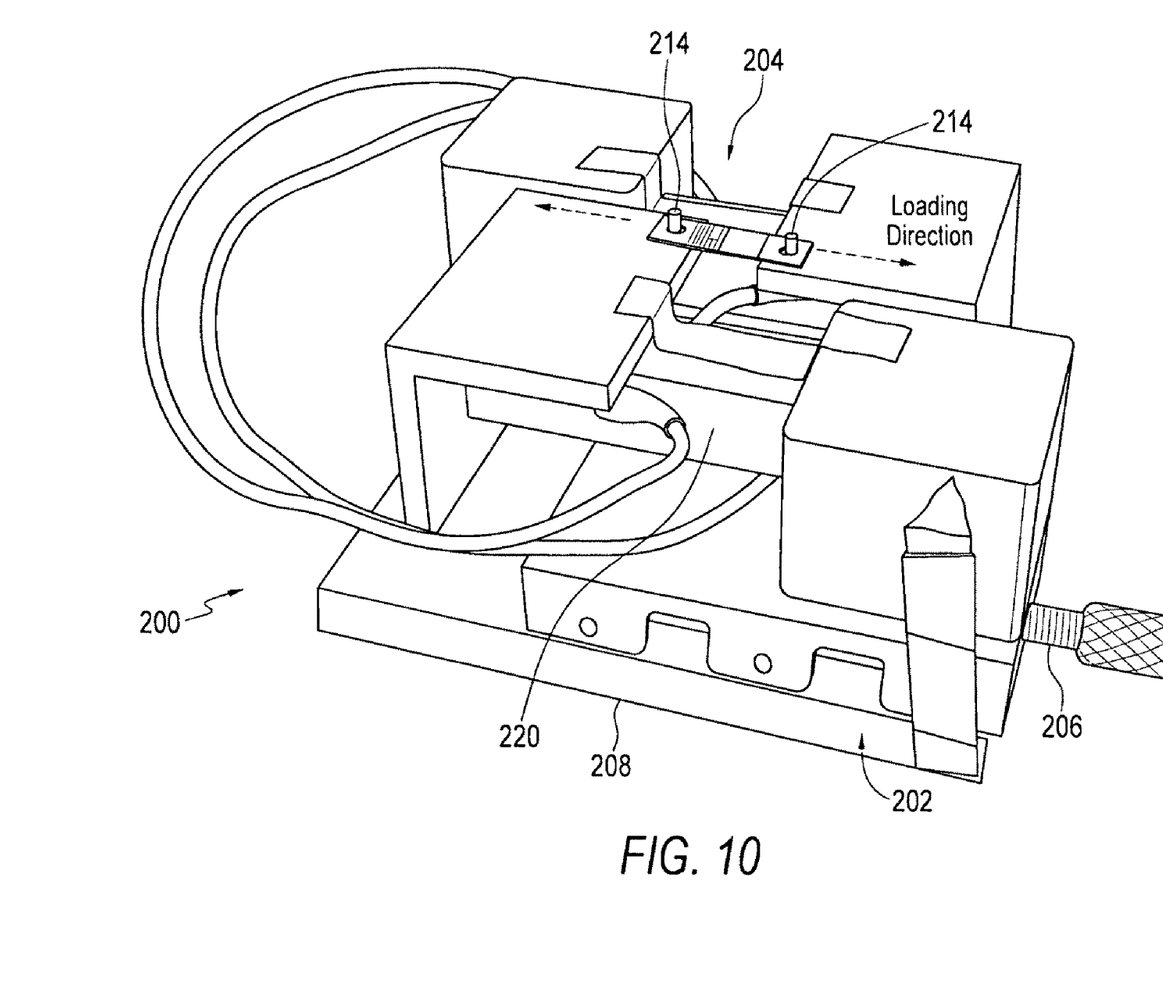
FIG. 10 shows a loading stage for receiving a testing stage, according to an embodiment of the present invention.

To actuate the testing stage 10 during material testing, a compact moving stage (straining stage) 200 is provided, as shown in FIG. 10. An example moving stage 200 has a size of 24 mm×50 mm×50 mm, allowing it to fit within a typical SEM chamber.

The moving stage 200 includes a pair of stages, particularly a coarse stage 202 and a fine stage 204. The coarse stage 202 may be, for example, a manual stage that is spring-loaded with a suitable spring 206 for coarse movement. A fixed platform 208 has a horizontal surface and a rail on which a spring-loaded platform is slidingly disposed. The fine stage 204 preferably is a piezo actuated stage. Two pillars 214 respectively disposed on first and second platforms are positioned to go through tear-drop loading holes 216 of the stage 10 for applying stage deformation. An adhesive may also be used to further secure the testing stage 10 to the first and second platforms, if needed. The fine stage 204 shown in FIG. 10 includes a pair of elongated piezo actuators 220 for moving the first and second platforms toward or away from one another. These piezo actuators have a small displacement range and high displacement resolution compared to that of the coarse stage 202. The coarse stage 202 and one of the piezo actuators 220 moves the first platform with respect to the second platform, while the other piezo actuator moves the second platform with respect to the first platform. Thus, both testing stages 202, 204 may be used to stretch or compress the testing stage 10 to apply load on the sample 44. The pair of longitudinally opposed tear-drop-shape loading holes 216 (see also FIG. 1) helps maintain the alignment between the sample 44 and the loading axis (displacement direction D).

During a test, the testing stage 10 is calibrated using the calibrator 150. For example, the calibrator 150 may be inserted into the calibration stage 170 for nanoindentation (precalibration). Then, the calibrator 150 is inserted into the opening 152 of the testing stage 10, for calibration. The externally fabricated sample 44 is inserted into the sample slot 40, 42. The testing stage 10 is positioned on the moving stage 200 so that the loading holes 216 are positioned around the pillars 214 of the platforms. Next, the coarse stage 202 is actuated, preferably at least to grip the testing stage 10 (i.e. so that the pillars 214 traverse their respective loading holes until they reach an edge of the loading holes). The coarse stage 202 may be further actuated until the testing stage 10 is sufficiently stretched or compressed to close the gap XX or X'X'. Next, the fine stage 204 is actuated to produce a tensile or compressive load on the sample 44. Particularly, the testing stage 10 is stretched by the fine actuator 204 for a tensile test or compressed for a compression test. The displacement gauges 70, 72, 76 are observed during tension or compression, and changes in the gaps $G_1$ and $G_2$ are measured. Separately or simultaneously, electrical resistance of the sample may be measured using contacts on the metal film 94 of the testing stage 10, as described above.

In an experimental operation of the example testing stage 10 and calibrator 150, a test sample is made by sectioning a bulk Rene N5 (single crystalline Ni superalloy), using FIB by a similar technique to that described in Uchich, M. D., Groeber, M. A., Dimiduk, D. M., and Simmons, J. P., Scripta Materialia, Vol. 55, No. 1, pp. 23-28, 2006. The sample is formed into a dogbone shape, having 20 μm-long gauge length, 10 μm thickness, and 5 μm width. Its composition is 30% Ni and 70% of $Ni_3Al$, where Ni is the solid solution matrix phase and $Ni_3Al$ is the precipitate. Sectioning by FIB is done so that the sample is oriented <111> out-of-plane on the top and slip lines are to form in <123> direction. Once the sample is separated from its bulk, it is transferred into the sample slot of the testing stage by a micromanipulator in FIB.

To apply tensile load on the sample in SEM, the compact moving stage 200 shown in FIG. 10 was provided. Its overall size is 24 mm×50 mm×50 mm to fit into the SEM chamber. The spring-loaded manual stage has a displacement resolution of 0.5 μm and maximum translation of 3 mm. The two piezo actuators each have maximum displacement of 10 μm.

The testing stage 10 is first placed on the moving stage 200 such that the two pillars 214 of the loading stage go through the holes 216 of the testing stage. The diameters of the pillar 214 and the hole 216 are 500 μm and 1000 μm, respectively. Thus, the pillars 214 need to travel by almost 1000 μm before the testing stage 10 can be gripped. The testing stage 10 then is stretched or compressed by another 50 μm to close gaps XX or X'X' before the sample can be loaded. This total travel of the pillars 214 is carried out by the spring-loaded manual stage 202. The entire setup is then moved to the SEM for in-situ loading of the sample using the piezo actuators 204.

The specimen 44 and the displacement gauges 70, 72, 76 are captured in the same image in SEM. Automated sequence of sample loading and image recording is used to stretch the specimen. The gauge displacement is measured by image auto-correlation technique to calculate the stress and strain of the sample. Microstructural change in the sample is correlated to the quantitative measurement of the mechanical response.

Figure 11:
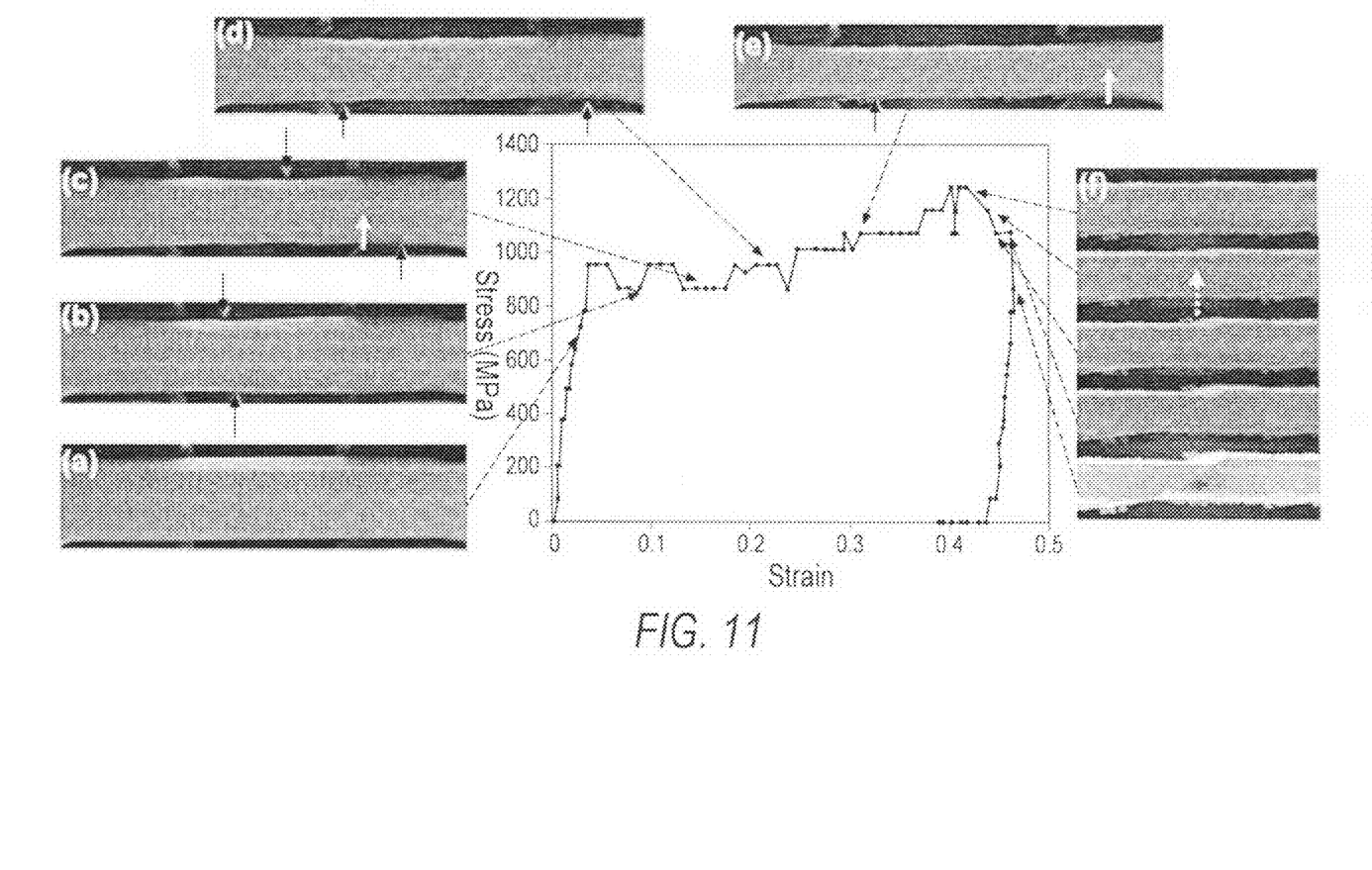
FIG. 11 shows results (plot of stress/strain behavior in correlation to microstructural change) of uniaxial tensile testing for a single crystal Ni superalloy sample.
Figure 12:
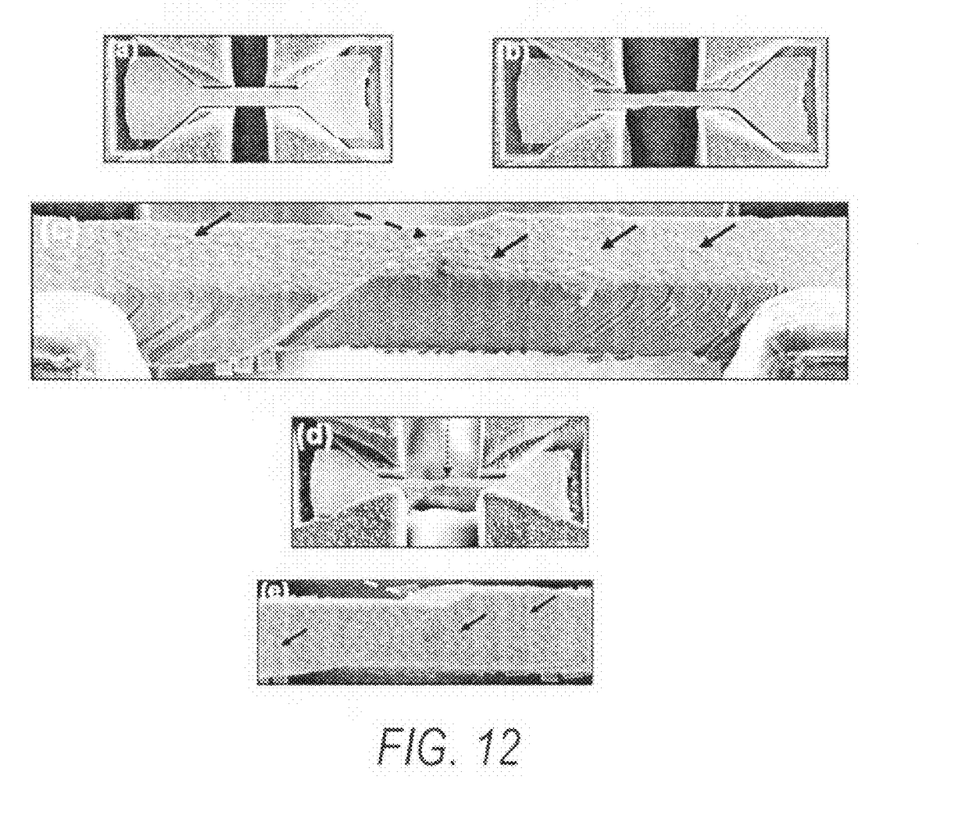
FIG. 12A shows an initial configuration of the sample.
FIG. 12B shows a final view of the sample after 40% of strain.
FIG. 12C shows a 30° tilt view of the sample in SEM, showing slip lines in the $1^{st}$ slip system (solid arrows) as well as another in the $2^{nd}$ slip system (dotted arrows) after strain.
FIG. 12D shows a tilted view of the entire sample after deformation.
FIG. 12E shows a top view of the sample after deformation showing multiple slips involved in the $2^{nd}$ slip system.

FIG. 11 shows the stress/strain response of the sample with corresponding microstructural evolution in SEM. It has an initial linear response giving an elastic modulus of 140 GPa and a yield strength of 1,000 MPa, similar to those found for a 5 μm-diameter pillar under compression in Uchic, M. D. and Dimiduk, D. M., Materials Science & Engineering A, Vol. 400-401, pp. 268-278, 2005. After yielding, there is significant plastic flow with little strain hardening up to about 25% strain. In-situ SEM observation reveals that during this deformation phase many slip lines are formed involving a single slip system, as shown in FIG. 12. The sample then begins to show strain hardening until about 40% strain, when the stress begins to drop. This peak stress coincides with the initiation of a second slip system, also shown in FIGS. 11 and 12. Multiple slips occur close to one another all involving this $2^{nd}$ slip system (shown at (e)), in contrast to uniformly distributed slips along the length of the sample in the $1^{st}$ slip system. The compression test, as described in Uchic and Dimiduk, on 5 μm-diameter pillar shows similar stress/strain characteristics. Here, ex-situ observation of the pillar after deformation showed $2^{nd}$ slip system, one of which was possibly activated at a higher strain.

One skilled in the art will appreciate that a method and apparatus for microscale and nanoscale testing of a sample has been shown and described, which provides a number of benefits. The testing stage allows measurement of stress-strain response of externally fabricated microscale samples of any materials that can be shaped into a dogbone. An example testing stage allows both tensile and compressive testing, as well as electrical resistivity testing, including during tension or compression. The testing stage can be reused if desired. Misalignment of tensile or compressive force is minimized, allowing for true uniaxial testing. Calibration of the testing stage can be performed simply and accurately, with fewer required components than in some previous calibration systems.

The size of an overall material testing system, including the testing stage, sample, calibrator, and moving stage, can be made relatively small so that tests can be carried out in situ. Accordingly, in situ observation of microstructure can be observed to correlate with corresponding stress-strain response. Additionally, by performing experiments inside an environmental cell, such as SEM, TEM, or other microscope such as an optical microscope, one can test the effect of environmental conditions.

While various embodiments of the present invention have been shown and described, it should be understood that other modifications, substitutions, and alternatives are apparent to one of ordinary skill in the art. Such modifications, substitutions, and alternatives can be made without departing from the spirit and scope of the invention, which should be determined from the appended claims.

Various features of the invention are set forth in the appended claims.

What is claimed is:

1. A system for testing a microscale or nanoscale sample, the system comprising:
   a testing stage comprising:
      a frame having first and second opposing ends and first and second side beams;
      at least one deformable force sensor beam near the first opposing end extending laterally across said frame between the first and second side beams;
      a first longitudinal beam bisecting said at least one force sensor beam, said first longitudinal beam having a free end;
      a second longitudinal beam having a free end facing the free end of said first longitudinal beam to define a gap therebetween;
      a support structure near the second opposing end, said support structure comprising a plurality of laterally extending beams disposed such that said second longitudinal beam bisects the plurality of laterally extending beams;
      a pair of slots, one disposed at each of the free ends of said first and second longitudinal beams respectively, each of the slots comprising a tapered portion leading to a generally longitudinal portion aligned with said first and second longitudinal beams, wherein said pair of slots together provide a seat for a dogbone-shaped sample; and
      a first opening disposed near the first opposing end and a second opening disposed near the second opposing end;
   a dog-bone shaped sample, said sample comprising opposed ends shaped to fit respectively within the slots and a longitudinal beam of said sample disposed between the opposed ends;
   a moving stage comprising a pair of inserts coupled to each of the pair of openings, respectively, said moving stage comprising at least one actuator coupled to at least one of the pair of inserts for moving the pair of inserts with respect to one another, thus placing a tensile or compressive load on said sample; and
   a calibrator coupled to and receivable within an opening in the second opposing end, said calibrator comprising:
      at least one leaf spring extending laterally across said calibrator;
      a longitudinal beam of said calibrator extending through said at least one leaf spring and bisecting said at least one leaf spring;
      a gauge longitudinally opposing said longitudinal beam of said calibrator and separated from said longitudinal beam of said calibrator by a gap; and
      a calibration support stage, said calibration support stage comprising a horizontal surface for supporting an end of said calibrator and a pair of vertical surfaces disposed normal to and over the horizontal surface for sandwiching said calibrator therebetween, at least one of the pair of vertical surfaces being movable relative to the horizontal surface.

2. The system of claim 1, wherein said moving stage comprises:
   a coarse stage;
   a fine stage having a displacement resolution finer than a displacement resolution of said coarse stage, said fine stage having at least one piezo actuator and at least one of the pair of inserts.

3. The system of claim 1, wherein said calibrator further comprises:
   at least one guide for mating with a guide fit at an inner portion of the opening;
   a teardrop-shaped loading hole disposed within said calibrator.

4. A method for placing a microscale or nanoscale sample under a tensile or compressive load, the method comprising:
   providing a testing stage, the testing stage comprising a frame having first and second opposing ends and first and second side beams, at least one deformable force sensor beam near the first opposing end extending laterally across said frame between the first and second side beams, a first longitudinal beam bisecting said at least one force sensor beam, said first longitudinal beam having a free end, a second longitudinal beam having a free end facing the free end of said first longitudinal beam to define a gap therebetween, a support structure near the second opposing end, said support structure comprising a plurality of laterally extending beams disposed such that said second longitudinal beam bisects the plurality of laterally extending beams, and a pair of slots, one disposed at each of the free ends of said first and second longitudinal beams respectively, each of the slots comprising a tapered portion leading to a generally longitudinal portion aligned with said first and second longitudinal beams, wherein said pair of slots together provide a seat for a dogbone-shaped sample;

inserting the sample into the pair of slots, wherein the sample comprises a dog-bone shape having a longitudinal portion shaped to fit into the generally longitudinal portion of each of the pair of slots and bridge the gap, and ends extending laterally from the longitudinal portion of the sample and shaped to fit into the tapered portion of each of the slots;

attaching a first end of the testing stage to the first end of a straining stage, and a second end of the testing stage to the second end of the straining stage;

actuating the straining stage to move the first and second ends of the straining stage with respect to one another;

determining a displacement of the force sensor beam;

determining a displacement of one of the first end of the testing stage and the second end of the testing stage;

calibrating a calibrator using a nanoindenter;

inserting the calibrator into an opening of the testing stage; and calibrating the at least one deformable force sensor beam with the calibrator.

5. The method of claim 4, wherein the sample is between one-half and 20 microns in length.

6. The method of claim 4, further comprising:

passing a current through at least one resistor on the testing stage and through the sample;

determining an electrical resistance of the sample.

* * * * *